United States Patent
Forsberg

(10) Patent No.: US 7,865,246 B2
(45) Date of Patent: Jan. 4, 2011

(54) OPTICAL COMMUNICATION OF NEUROSTIMULATION-SYSTEM INFORMATION

(75) Inventor: John W. Forsberg, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 320 days.

(21) Appl. No.: 11/445,655

(22) Filed: Jun. 2, 2006

(65) Prior Publication Data

US 2007/0010858 A1 Jan. 11, 2007

Related U.S. Application Data

(62) Division of application No. 10/132,122, filed on Apr. 25, 2002, now Pat. No. 7,076,292.

(51) Int. Cl.
*A61N 1/05* (2006.01)

(52) U.S. Cl. .......................... 607/115; 607/2

(58) Field of Classification Search ................ 607/60, 607/115
See application file for complete search history.

(56) References Cited

U.S. PATENT DOCUMENTS

| | | | |
|---|---|---|---|
| 4,432,363 A | | 2/1984 | Kakegawa |
| 4,612,934 A | * | 9/1986 | Borkan .................. 607/62 |
| 4,877,032 A | | 10/1989 | Heinze |
| 5,174,288 A | | 12/1992 | Bardy et al. |
| 5,217,010 A | | 6/1993 | Tsitlik |
| 5,370,672 A | | 12/1994 | Fowler et al. |
| 5,454,837 A | * | 10/1995 | Lindegren et al. ............ 607/9 |
| 5,617,235 A | | 4/1997 | Abrahamson |
| 5,925,068 A | | 7/1999 | Kroll |
| 5,944,746 A | * | 8/1999 | Kroll ........................ 607/27 |
| 5,995,860 A | | 11/1999 | Sun |
| 6,091,015 A | | 7/2000 | del Valle |
| 6,238,420 B1 | | 5/2001 | Bakels et al. |
| 6,575,965 B1 | * | 6/2003 | Fitch et al. .................. 606/15 |
| 6,668,193 B2 | | 12/2003 | Ware et al. |
| 6,795,736 B2 | * | 9/2004 | Connelly et al. ............ 607/36 |

(Continued)

FOREIGN PATENT DOCUMENTS

EP 1181947 A2 2/2002

(Continued)

OTHER PUBLICATIONS

PCT International Search Report, International Application No. PCT/US03/08077, 3 pages.

*Primary Examiner*—Carl H Layno
*Assistant Examiner*—Brian T Gedeon
(74) *Attorney, Agent, or Firm*—Banner & Witcoff, Ltd.

(57) ABSTRACT

A neurostimulation lead includes fiber optic cable. A human-implantable neurostimulator and neurostimulation lead each include an opto-electric transducer. The opto-electric transducers can be an optical transmitter, an optical receiver, or an optical transducer, that converts: electrical energy to optical energy; optical energy to electrical energy; or both electrical energy to optical energy and optical energy to electrical energy. Neurostimulation-lead electrodes can be activated, and/or lead-status information can be transmitted, over the fiber optic cable, between the neurostimulator and the neurostimulation lead. A neurostimulation-lead power converter may be coupled to a pulse generator of the neurostimulator such that the power converter derives and stores power for the lead from stimulation pulses received from the stimulation-pulse generator.

8 Claims, 5 Drawing Sheets

U.S. PATENT DOCUMENTS

| | | |
|---|---|---|
| 6,898,464 B2 * | 5/2005 | Edell et al. .................... 607/60 |
| 7,305,268 B2 * | 12/2007 | Gliner et al. .................. 607/45 |
| 2002/0107557 A1 | 8/2002 | Edell |
| 2002/0156512 A1 | 10/2002 | Borkan |
| 2002/0156513 A1 | 10/2002 | Borkan |
| 2003/0036776 A1 | 2/2003 | Foster |
| 2003/0083724 A1 | 5/2003 | Jog |
| 2004/0127965 A1 | 7/2004 | Borkan |

FOREIGN PATENT DOCUMENTS

| | | |
|---|---|---|
| EP | 1181948 A2 | 2/2002 |
| JP | 5245215 | 9/1993 |
| WO | 9312724 | 7/1993 |
| WO | 0042914 | 7/2000 |
| WO | 03059445 | 7/2003 |

* cited by examiner

US 7,865,246 B2

OPTICAL COMMUNICATION OF NEUROSTIMULATION-SYSTEM INFORMATION

This Application is a divisional of U.S. application Ser. No. 10/132,122, filed Apr. 25, 2002, now U.S. Pat. No. 7,076,292, which is incorporated by reference in its entirety herein.

FIELD OF THE INVENTION

The invention relates to communicating information within a human-implantable neurostimulation system and more particularly to optical communication of control and status information within such a system.

BACKGROUND OF THE INVENTION

The number of neurostimulation-electrode wires and their combined diameter often limits the number of electrodes that can be included in a neurostimulation lead. Further, electrically conductive electrode wires are susceptible to electromagnetic interference (EMI). Accordingly, reducing the number of electrode wires, their combined diameter, and their susceptibility to EMI would be desirable.

BRIEF SUMMARY OF THE INVENTION

According to various illustrative embodiments of the invention, a human-implantable neurostimulation system overcomes the shortcomings associated with electrically conductive-electrode wires discussed above, by using optical fiber in a neurostimulation lead. The implantable neurostimulation system may include a neurostimulator having a power source, a processor, a stimulation-pulse generator, and an opto-electric transducer.

The opto-electric transducer can be any device, such as an optical transmitter, an optical receiver, or an optical transducer, that converts: (1) electrical energy to optical energy; (2) optical energy to electrical energy; or (3) both electrical energy to optical energy and optical energy to electrical energy. The opto-electric transducer can include an optical transmitter and/or an optical receiver.

A neurostimulation-lead power converter may be coupled to a neurostimulator pulse generator via electrical conductors and an electrical connector. The power converter can then derive and store power for the lead from therapeutic and/or non-therapeutic stimulation pulses that the power converter receives from the stimulation-pulse generator or though a direct electrical connection to the neurostimulator power source.

Sensor circuitry within the lead may include one or more sensors for sensing conditions related to lead-system status. These conditions may include electrode impedance, temperature, pH, electrical activity at the electrode, neurological, and/or other desired physiological electrical measurements.

In accordance with an embodiment of the invention, a method of controlling activation of at least one electrode of a neurostimulation lead includes transmitting optically-coded information that specifies, at least in part, one or more electrodes of a neurostimulation lead to which neurostimulation pulses are directed. Similar methods, in accordance with additional embodiments, are directed to communicating information from a neurostimulation lead to a neurostimulator and to a method of communicating information bi-directionally between a neurostimulation lead and a pulse generator in accordance with various embodiments of the invention.

DETAILED DESCRIPTION OF THE INVENTION

Figure 1:
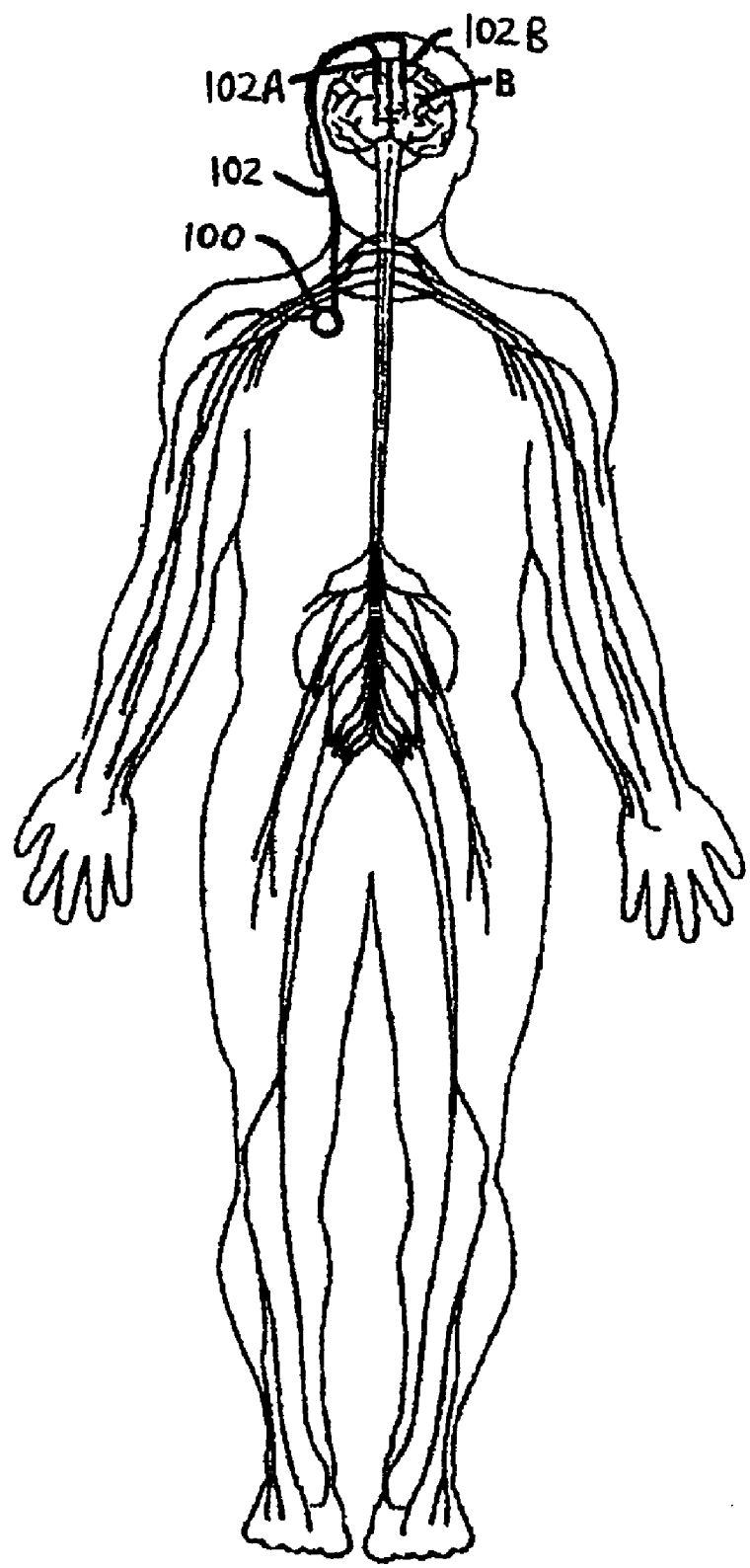
FIG. 1 depicts a neurostimulation system implanted in a person's body in accordance with an illustrative embodiment of the invention.

FIG. 1 depicts a microprocessor-controlled neurostimulator 100 in accordance with an illustrative embodiment of the invention. Neurostimulator 100 may be implanted below the skin of a patient, or alternatively, may be an external device. The human-implantable neurostimulator 100 may take the form of a modified signal generator Model 7424 manufactured by Medtronic, Inc. under the trademark Itrel II®. Lead 102 may be any lead suitable for stimulation and may, as described in more detail below, include fiber optic cable. The lead 102 may be positioned to stimulate tissue at various locations within the patient's body, including one or more specific sites in the patient's brain B. The lead 102 may be divided into multiple distal ends, such as lead ends 102A and 102B. Lead distal ends of this type may include one or more stimulation electrodes and may be implanted, by conventional stereotactic surgical techniques, into a portion of the brain such as the thalamus, the internal capsule, the globus pallidus, the subthalamic nucleus, or other neural structure. Lead ends 102A and 102B may be surgically implanted through a hole in a patient's skull and a remaining portion of lead 102 may be implanted between the patient's skull and scalp.

Figure 2:
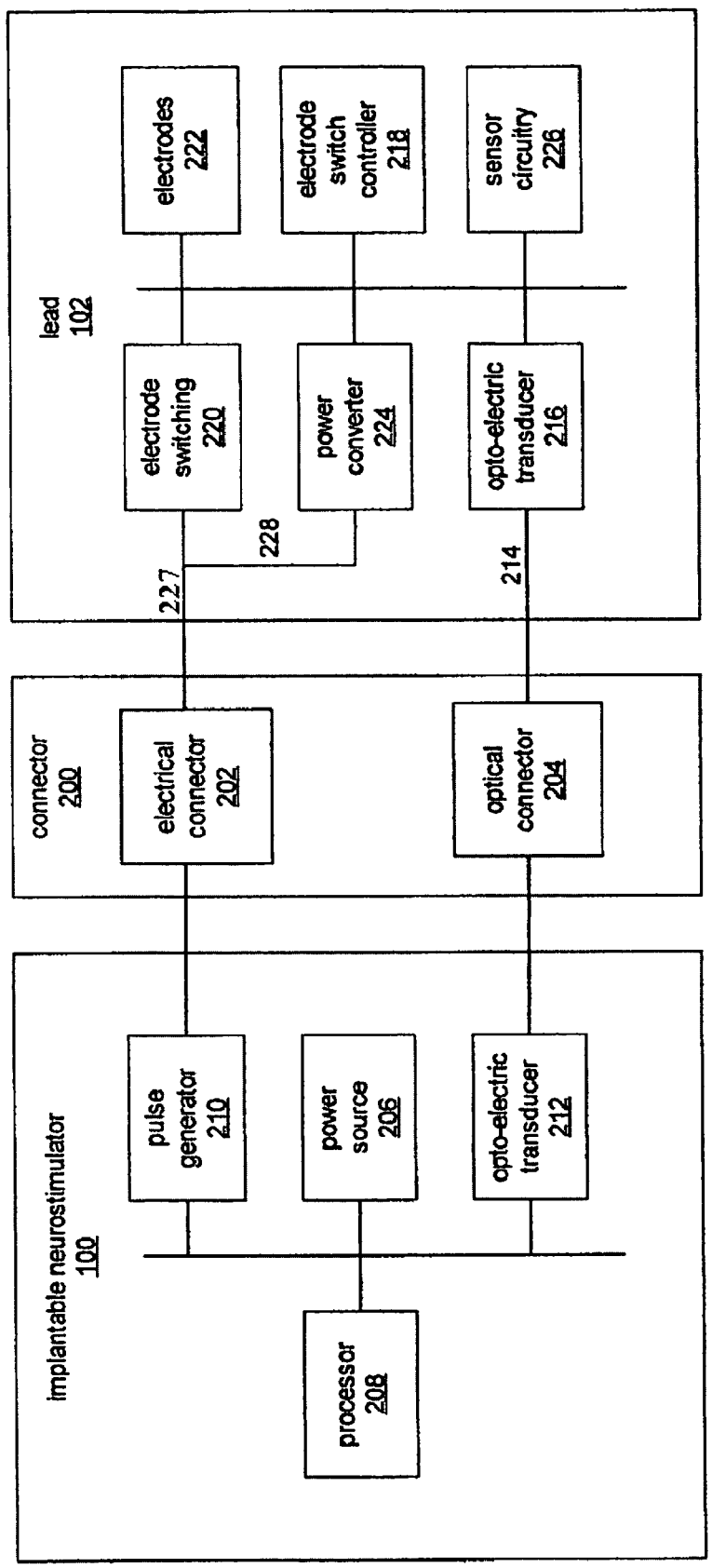
FIG. 2 is a schematic diagram of a neurostimulation system in accordance with an illustrative embodiment of the invention.

FIG. 2 is a schematic diagram of a neurostimulation system in accordance with an illustrative embodiment of the invention. The human-implantable neurostimulator 100 is coupled via a connector 200, which may include an electrical connector 202 and/or an optical connector 204, which may be a quartz-type feedthrough, to a neurostimulation lead 102. The implantable neurostimulator 100 may include a power source 206, a processor 208, a stimulation-pulse generator 210, and an opto-electric transducer 212.

Opto-electric transducer 212 can be any device, such as an optical transmitter, an optical receiver, or an optical transducer, that converts: (1) electrical energy to optical energy; (2) optical energy to electrical energy; or (3) both electrical energy to optical energy and optical energy to electrical energy. Opto-electric transducer 212 can include an optical transmitter, which may, in turn, include any suitable light source, such as an LED (light-emitting diode). In addition, or alternatively, opto-electric transducer 212 can include an optical receiver, which, in turn, may include a light receiver, such as a photo-diode.

The processor 208 may be a microprocessor, a microcontroller, a digital signal processor, or the like. The stimulation-pulse generator 210 may be any device that generates therapeutic stimulation pulses. For instance, the stimulation-pulse generator 210 may be a signal generator of the type used in the Model 7424 manufactured by Medtronic, Inc. under the trademark Itrel II®.

Neurostimulation lead 102 may include a fiber-optic cable 214 and an opto-electric transducer 216. Like opto-electric transducer 212, opto-electric transducer 216 can be any device that converts: (1) electrical energy to optical energy; or (2) optical energy to electrical energy; or (3) both electrical energy to optical energy and optical energy to electrical energy. Opto-electric transducer 216 can include an optical transmitter, which may, in turn, include any suitable light source, such as an LED (light-emitting diode). In addition, or alternatively, opto-electric transducer 216 can include an optical receiver, which in turn may include a light receiver, such as a photo-diode.

Opto-electric transducer 212 may transmit coded control information over the fiber-optic cable 214 to the opto-electric transducer 216. The opto-electric transducer 216 may then send the coded control information to an electrode switch controller 218. The output of the electrode switch controller 218 may then be input to the electrode-switching module 220 for coupling stimulation pulses from the stimulation-pulse generator 210 of the implantable neurostimulator 100 to one or more of electrodes 222 based on the coded control information transmitted over the fiber-optic cable 214. In this way, processor 208 can communicate over fiber optic cable 214 information specifying which of the electrodes 222 should be activated at particular times.

A power converter 224 may be coupled to the pulse generator 210 via electrical conductors 227 and 228 and electrical connector 202. The power converter 224 can then derive and store power for the lead's electrical components directly from theraputic stimulation pulses or from non-theraputic stimulation pulses sent during time intervals when the stimulation-pulse generator is not sending therapeutic stimulation pulses.

Sensor circuitry 226 may include one or more sensors for sensing conditions related to lead system status, which may include, but is not limited to, electrode impedance, temperature, electrical activity at the electrodes, pH, neurological, and/or other desired physiological electrical measurements. Many sensors for sensing this type of information are well known in the art. Sensor circuitry 226 may also include associated control circuitry for providing sensed information to the opto-electric transducer 216. Opto-electric transducer 216 can then send this information over the fiber optic cable 214 to the implantable neurostimulator 100.

Figure 3:
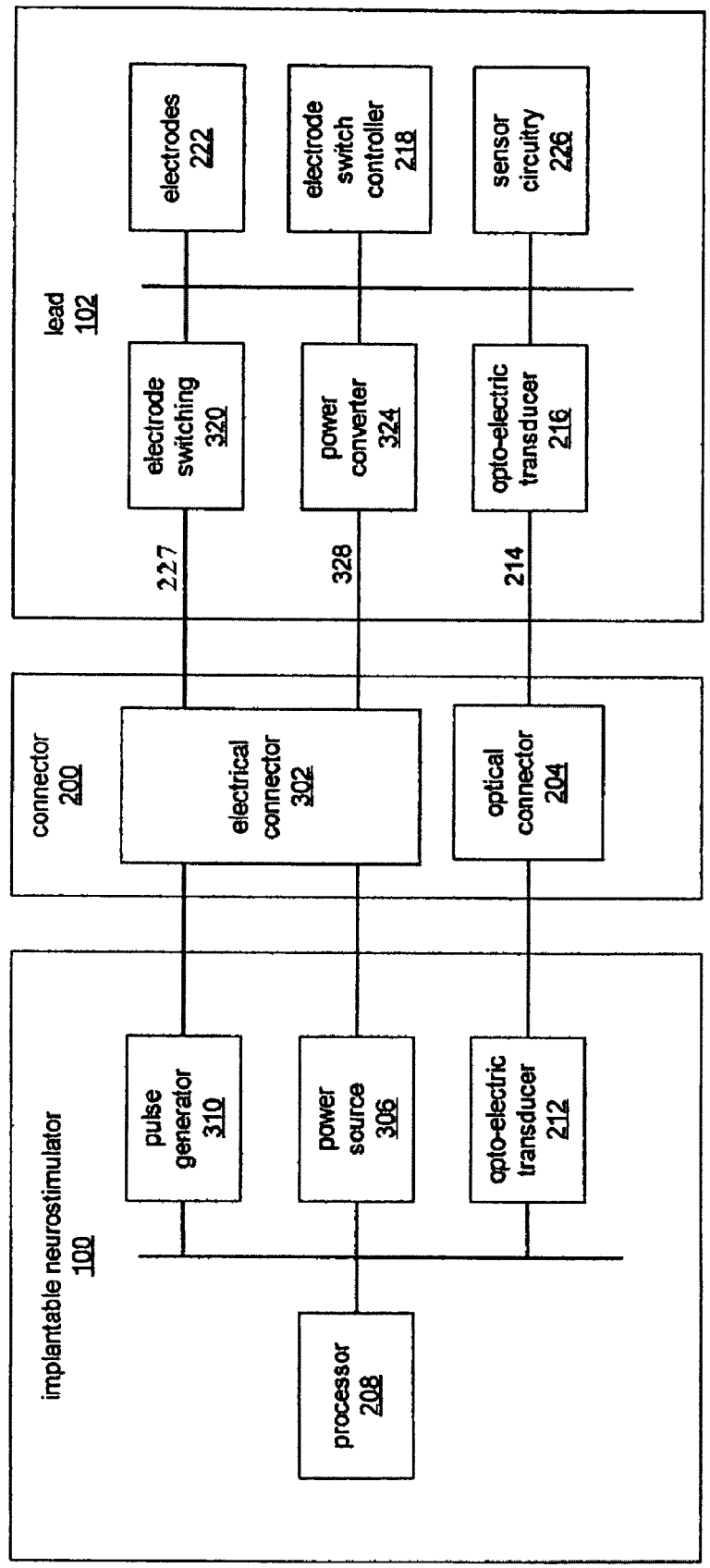
FIG. 3 is a schematic diagram of a neurostimulation system that is similar to the system of FIG. 2 wherein electrical power is transfer to the neurostimulation lead is accomplished differently.

FIG. 3 shows an embodiment of the invention that is similar to the embodiment shown in FIG. 2 except that a power converter 324 is coupled more directly, via electrical conductors 328 and an electrical connector 302, to a power source 306 of the neurostimulator 100. In this embodiment, the power converter 324 therefore receives power more directly from the power source 306 rather than deriving power through stimulation pulses.

Figure 4:
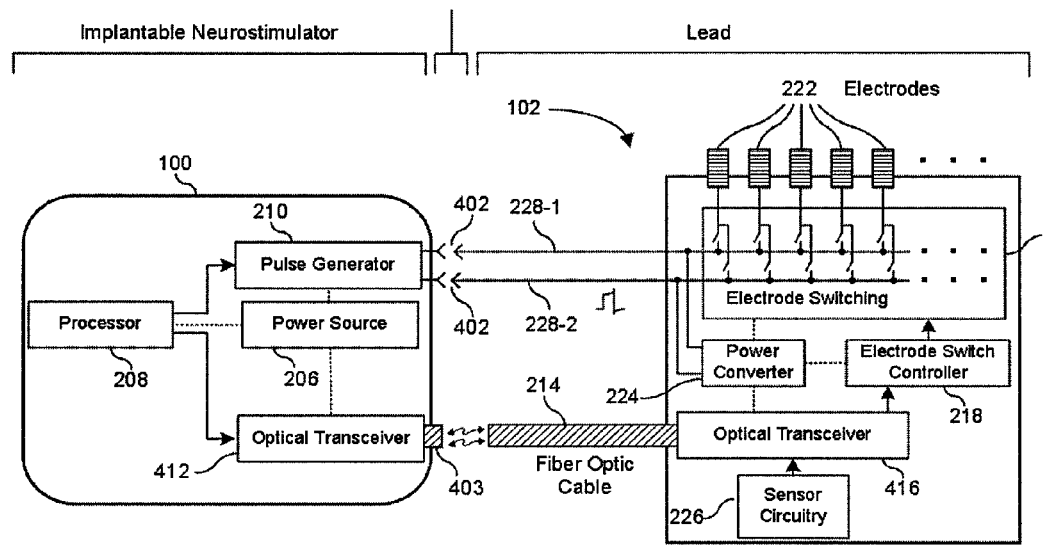
FIG. 4 depicts an embodiment of the invention in which power is supplied from the neurostimulator to the neurostimulation lead via stimulation pulses.

FIG. 4 depicts an embodiment of the invention in which power is supplied from the neurostimulator 100 to the neurostimulation lead 102 via stimulation pulses, as discussed above in connection with the embodiment shown in FIG. 2. A light source 403 of an optical transceiver 412 of neurostimulator 100 may transmit coded control information over the fiber-optic cable 214 to an optical transceiver 416 of the neurostimulation lead 102. The optical transceiver 416 may then send the coded control information to an electrode switch controller 218. The output of the electrode switch controller 218 is then input into the electrode-switching module 220 for coupling stimulation pulses from the stimulation-pulse generator 210 of the implantable neurostimulator 100 to one or more of electrodes 222 based on the coded control information transmitted over the fiber-optic cable 214. In this way, processor 208 can communicate over fiber optic cable 214 information specifying which of electrodes 222 should be activated at particular times.

The power converter 224 may be coupled to the pulse generator 210 via conductors 228-1 and 228-2 and connectors 402 to the implantable neurostimulator 100. The power converter 224 can then derive and store power for the lead 102 from stimulation pulses that the power converter 224 receives from the stimulation-pulse generator 210.

Sensor circuitry 226 may include one or more sensors for sensing conditions related to lead system status, which may include electrode impedance, temperature, pH, neurological and/or other desired physiological electrical measurements. Many sensors for sensing this type of information are well known in the art. Sensor circuitry 226 may also include associated control circuitry for providing sensed information to the optical transceiver 416. Optical transceiver 416 may then send this information over the fiber optic cable 214 to the implantable neurostimulator 100.

Figure 5:
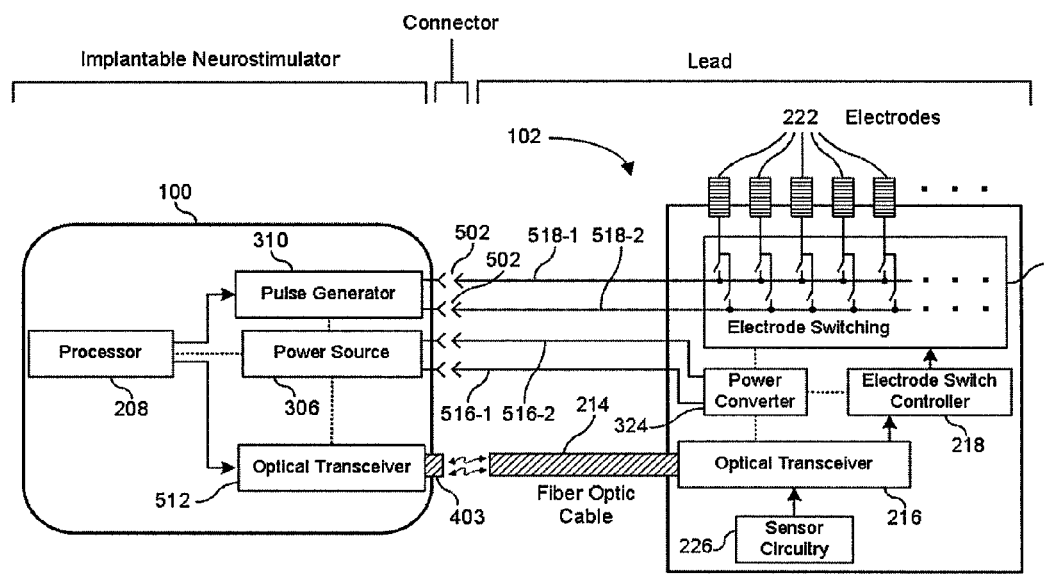
FIG. 5 depicts an embodiment of the invention in which power is supplied from the neurostimulator to the neurostimulation lead via electrical conductors.

FIG. 5 depicts an embodiment of the invention in which power is supplied from the neurostimulator 100 to the neurostimulation lead 102 via conductors 516-1 and 516-2 connected to power source 306 in a manner similar to what was discussed above in connection with the embodiment shown in FIG. 3. The pulse generator 310 can be connected to the electrodes 222 via connectors 502 and conductors 518-1, 518-2. As in FIG. 4, an optical transceiver 512 is provided for transmitting coded control information over the fiber-optic cable 214.

Figure 6:
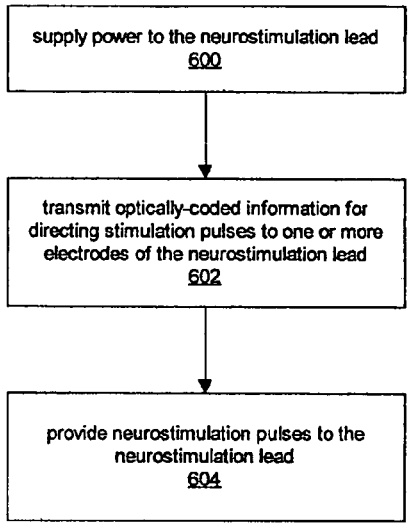
FIG. 6 depicts steps of a method of controlling activation of at least one electrode of a neurostimulation lead in accordance with an embodiment of the invention.

FIG. 6 depicts steps of a method of controlling activation of at least one electrode of a neurostimulation lead in accordance with an embodiment of the invention. As shown in step 600, power is supplied to the neurostimulation lead. Any suitable technique can be used for supplying power to the neurostimulation lead, such as coupling a power converter to a neurostimulator power source as discussed above, which may include the power converter deriving power from neurostimulation pulses. Step 602 is directed to transmitting optically-coded information that specifies, at least in part, one or more electrodes of the neurostimulation lead to which the neurostimulation pulses are directed. Therapeutic neurostimulation pulses are then sent to the lead and are directed to the specified electrode or electrodes, as shown in step 604.

Figure 7:
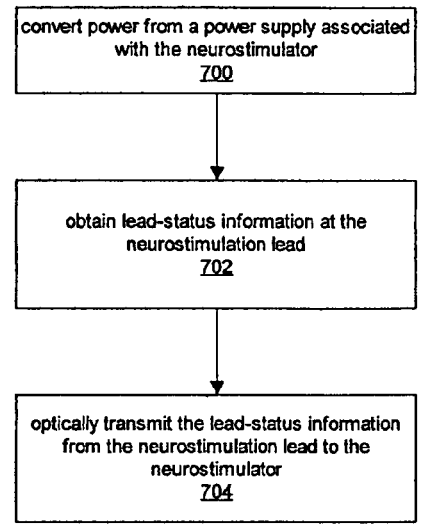
FIG. 7 depicts steps of a method of communicating information from a neurostimulation lead to a neurostimulator in accordance with an embodiment of the invention.

FIG. 7 depicts steps of a method of communicating information from a neurostimulation lead to a neurostimulator in accordance with an embodiment of the invention. As shown in step 700, power, from a power supply associated with the neurostimulator, is converted, such as by deriving power from neurostimulation pulses. Lead-status information, which may include electrode impedance, temperature, pH, neurological and/or other desired physiological electrical measurements, is obtained at the neurostimulation lead, as shown in step 702. Step 704 is directed to optically transmitting the lead-status information from the neurostimulation lead to the neurostimulator.

Figure 8:
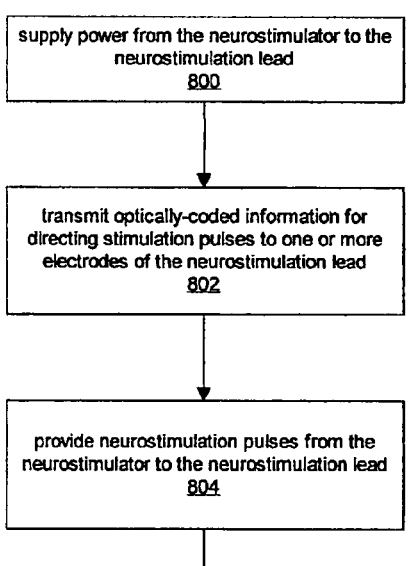
FIG. 8 depicts steps of a method of communicating information between a neurostimulation lead and a neurostimulator in accordance with an embodiment of the invention.
Figure 8:
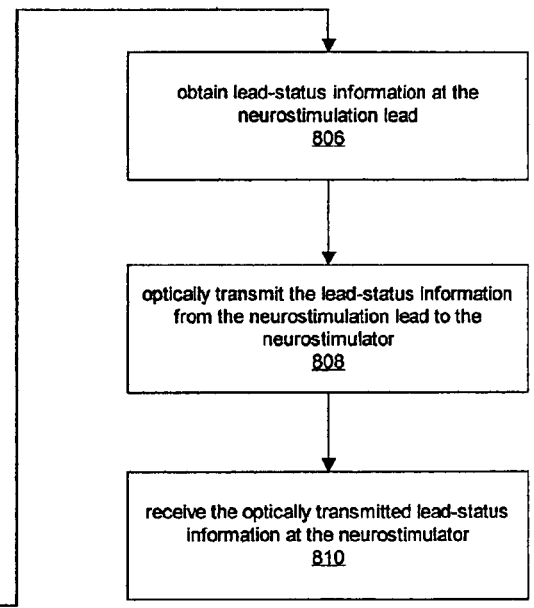

FIG. 8 depicts steps of a method of communicating information between a neurostimulation lead and a neurostimulator in accordance with an embodiment of the invention. As shown in step 800, power is supplied from a power supply associated with the neurostimulator to the neurostimulation lead. Any suitable technique can be used for supplying power to the neurostimulation lead, such as coupling a power converter to a neurostimulator power source as discussed above, which may include the power converter deriving power for the lead from neurostimulation pulses. Step 802 is directed to transmitting optically-coded information that specifies, at least in part, one or more electrodes of the neurostimulation lead to which the neurostimulation pulses are directed. Therapeutic neurostimulation pulses are then sent to the lead and are directed to the specified electrode or electrodes, as shown in step 804.

Lead-status information, which may include electrode impedance, temperature, pH, neurological and/or other desired physiological electrical measurements, is obtained at the neurostimulation lead, as shown in step 806. Steps 808 and 810 are directed to optically transmitting the lead-status information from the neurostimulation lead and receiving the lead-status information at the neurostimulator, respectively.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

I claim:

1. A method of controlling activation of at least one electrode of an implantable neurostimulation lead in a neurostimulation system, wherein the neurostimulation system includes an implantable neurostimulator and the implantable neurostimulation lead, the method comprising:
   supplying electrical power from a power source associated with the implantable neurostimulator to the implantable neurostimulation lead;
   providing neurostimulation pulses from an electrical pulse generator associated with the implantable neurostimulator to the implantable neurostimulation lead over at least two electrical conductors, wherein the at least two electrical conductors connect the electrical pulse generator to the implantable neuro stimulation lead;
   transmitting optically-coded information via a fiber optic cable from an opto-electric transducer associated with the implantable neurostimulation lead that specifies, at least in part, one or more electrodes of the implantable neurostimulation lead to which the neurostimulation pulses are directed; and
   coupling in the implantable neurostimulation lead, by an electrode-switching module, the neurostimulation pulses to the one or more electrodes based on the optically-coded information received via the fiber optic cable.

2. The method of claim 1 wherein supplying electrical power to the neurostimulation lead further comprises providing power to the neurostimulation lead via the neurostimulation pulses provided over the at least two electrical conductors.

3. The method of claim 1, wherein the neurostimulator is adapted to be implanted below the skin of a patient.

4. A method of communicating information between an implantable neurostimulation lead and an implantable pulse generator, wherein a neurostimulation system comprises an implantable neurostimulator and the implantable neurostimulation lead, the method comprising:
   supplying electrical power from a power source associated with the implantable neurostimulator to the implantable neurostimulation lead;
   providing neurostimulation pulses from an electrical pulse generator associated with the implantable neurostimulator to the implantable neurostimulation lead over at least two electrical conductors, wherein the at least two electrical conductors connect the implantable neurostimulator to the implantable neurostimulation lead;
   transmitting optically-coded information via a fiber optic cable from an opto-electric transducer associated with the implantable neurostimulation lead that specifies, at least in part, one or more electrodes of the implantable neurostimulation lead to which the neurostimulation pulses are directed;
   coupling in the implantable neurostimulation lead, by an electrode-switching module, the neurostimulation pulses to the one or more electrodes based on the optically-coded information received via the fiber optic cable;
   obtaining lead-status information at the implantable neurostimulation lead;
   optically transmitting the lead-status information via the fiber optic cable from the implantable neurostimulation lead to the implantable neurostimulator, wherein the lead-status information is optically transmitted from a first optical transceiver associated with the implantable neurostimulation lead; and
   receiving the optically transmitted lead-status information via the fiber optic cable at the implantable neurostimulator, where in the lead-status information is optically received from a second optical transceiver associated with the implantable neurostimulator.

5. The method of claim 4 wherein supplying electrical power to the neurostimulation lead further comprises providing power to the neurostimulation lead via the neurostimulation pulses provided over the at least two electrical conductors.

6. The method of claim 4, wherein the lead-status information includes information from at least one sensor.

7. The method of claim 4, wherein the neurostimulator is adapted to be implanted below the skin of a patient.

8. The method of claim 4, wherein the lead-status information is selected from the group consisting of: electrode impedance, temperature, electrode electrical activity, and pH.

* * * * *